United States Patent
Azar

(10) Patent No.: US 9,373,166 B2
(45) Date of Patent: Jun. 21, 2016

(54) REGISTERED VIDEO ENDOSCOPY AND VIRTUAL ENDOSCOPY

(75) Inventor: Fred S. Azar, Princeton, NJ (US)

(73) Assignee: SIEMENS MEDICAL SOLUTIONS USA, INC., Malvern, PA (US)

(*) Notice: Subject to any disclaimer, the term of this patent is extended or adjusted under 35 U.S.C. 154(b) by 2116 days.

(21) Appl. No.: 11/108,440

(22) Filed: Apr. 18, 2005

(65) Prior Publication Data

US 2005/0251017 A1 Nov. 10, 2005

Related U.S. Application Data

(60) Provisional application No. 60/564,936, filed on Apr. 23, 2004.

(51) Int. Cl.
| | |
|---|---|
| *A61B 5/05* | (2006.01) |
| *G06T 7/00* | (2006.01) |
| *A61B 1/00* | (2006.01) |
| *A61B 5/06* | (2006.01) |

(52) U.S. Cl.
CPC ............ *G06T 7/0012* (2013.01); *A61B 1/00158* (2013.01); *A61B 5/06* (2013.01); *A61B 90/36* (2016.02); *G06T 7/0018* (2013.01); *A61B 2034/2072* (2016.02); *G06T 2200/04* (2013.01); *G06T 2207/30028* (2013.01)

(58) Field of Classification Search
USPC ................................ 600/407–480, 173; 606/2
See application file for complete search history.

(56) References Cited

U.S. PATENT DOCUMENTS

| | | | | |
|---|---|---|---|---|
| 5,704,791 | A * | 1/1998 | Gillio .............................. | 434/262 |
| 5,724,978 | A * | 3/1998 | Tenhoff ......................... | 600/467 |
| 5,771,895 | A * | 6/1998 | Slager ............................ | 600/462 |
| 5,836,869 | A * | 11/1998 | Kudo et al. .................... | 600/173 |
| 5,879,297 | A | 3/1999 | Haynor et al. ................. | 600/407 |
| 5,953,013 | A * | 9/1999 | Shimizu ......................... | 345/419 |
| 6,019,725 | A * | 2/2000 | Vesely et al. ................... | 600/447 |
| 6,129,668 | A | 10/2000 | Haynor et al. ................. | 600/424 |
| 6,216,028 | B1 | 4/2001 | Haynor et al. ................. | 600/424 |
| 6,263,230 | B1 | 7/2001 | Haynor et al. ................. | 600/424 |
| 6,298,262 | B1 * | 10/2001 | Franck et al. ................. | 600/426 |
| 6,857,878 | B1 * | 2/2005 | Chosack et al. ............... | 434/267 |
| 6,863,536 | B1 * | 3/2005 | Fisher et al. ................... | 434/272 |
| 6,892,090 | B2 * | 5/2005 | Verard et al. ................... | 600/424 |
| 6,928,314 | B1 * | 8/2005 | Johnson et al. ................ | 600/407 |
| 2002/0198470 | A1 * | 12/2002 | Imran et al. .................... | 600/587 |
| 2003/0060702 | A1 * | 3/2003 | Kuth et al. ..................... | 600/424 |
| 2003/0160721 | A1 * | 8/2003 | Gilboa et al. .................. | 342/450 |
| 2005/0177054 | A1 * | 8/2005 | Yi et al. ......................... | 600/510 |

FOREIGN PATENT DOCUMENTS

DE    10 2004 011 155 A1    8/2005

* cited by examiner

*Primary Examiner* — Joel F Brutus

(57) ABSTRACT

An endo-robot can be tracked and a reconstructed 3D volume of data can be created for virtual endoscopy. The 3D position and orientation of each image captured by the endo-robot is determined. The longitudinal distance traveled inside the structure of interest is determined. The position, orientation and longitudinal distance are used to register the position of the endo-robot to a corresponding position inside the 3D volume of data. Virtual endoscopy can be used to locate areas of interest and correlate clinical findings with the images of the areas of interest.

10 Claims, 5 Drawing Sheets

REGISTERED VIDEO ENDOSCOPY AND VIRTUAL ENDOSCOPY

This application claims priority to U.S. Provisional Application Ser. No. 60/564,936, filed on Apr. 23, 2004, which is herein incorporated by reference in its entirety.

BACKGROUND OF THE INVENTION

1. Technical Field

The present invention relates to endoscopy, and more particularly to a system and method for externally tracked video endoscopy using endo-robots combined with virtual endoscopy.

2. Discussion of Related Art

Endoscopic examination is a medical procedure in which an imaging device referred to as an endoscope is inserted into a live subject for the purpose of diagnosis and/or treatment. Examples of endoscopy are the colonoscopy and bronchoscopy.

These procedures require that the instrument be inserted and controlled through direct mechanical interaction. This includes some portion of the instrument being inside the patient while the rest of the same instrument is manipulated externally. By necessity of design, most endoscopic devices are in the form of long flexible or rigid tubes attached to a control head that remains outside the body of the patient.

A consequence of this design is that there is usually some mild to severe discomfort associated with endoscopy coupled with a risk of damage to internal structures if too much force is applied externally to the endoscope.

Virtual endoscopy could in theory be used to explore the body structures of interest and to detect the problem areas, such as nodules or polyps. However, this technique can lead to the detection of false positives or misdiagnoses, which in turn can lead to unneeded invasive biopsies.

Therefore, a need exists for a system and method for an endo-robot.

SUMMARY OF THE INVENTION

According to an embodiment of the present disclosure, a computer-implemented method for associating an image with an area of interest in a three-dimensional volume includes modeling a volume as the three-dimensional volume, tracking an image capturing device within the volume, storing position and orientation information of the image capturing device at a time when at least one image is captured, and determining a longitudinal distance traveled by the image capturing device at the time when the at least one image is captured. The method further includes registering the position, orientation and longitudinal distance of the image capturing device to a corresponding position within the three-dimensional volume, determining an area of interest within the three-dimensional volume, and determining the at least one image registered to correspond to the area of interest, wherein the at least one image is displayed and the area of interest is characterized.

Registering further comprises determining a centerline of the three-dimensional volume, determining a correspondence between a track of the image capturing device and the centerline of the three-dimensional volume, and registering the at least one image to a position within the three-dimensional volume. Registering further comprises determining an initial position of the video capturing device and manually selecting a position corresponding to the initial position in the three-dimensional volume.

The longitudinal distance is a distance of the video capturing device from the initial position.

Determining the at least one image comprises automatically displaying the at least one image in conjunction with the display of the corresponding position within the three-dimensional volume.

According to an embodiment of the present disclosure, a program storage device is provided readable by machine, tangibly embodying a program of instructions executable by the machine to perform method steps for associating an image with an area of interest in a three-dimensional volume. The method steps including modeling a volume as the three-dimensional volume, tracking an image capturing device within the volume, storing position and orientation information of the image capturing device at a time when at least one image is captured, and determining a longitudinal distance traveled by the image capturing device at the time when the at least one image is captured. The method further includes registering the position, orientation and longitudinal distance of the image capturing device to a corresponding position within the three-dimensional volume, determining an area of interest within the three-dimensional volume, and determining the at least one image registered to correspond to the area of interest, wherein the at least one image is displayed and the area of interest is characterized.

According to an embodiment of the present disclosure, a method for viewing a virtual volume of a real space comprises displaying a portion of the virtual volume of the real space, displaying, automatically and simultaneously, a registered image of the real space corresponding to the portion of the virtual volume in a second window, and characterizing the portion of the virtual volume based on the combination of the virtual volume and the registered image.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

Figure 1:
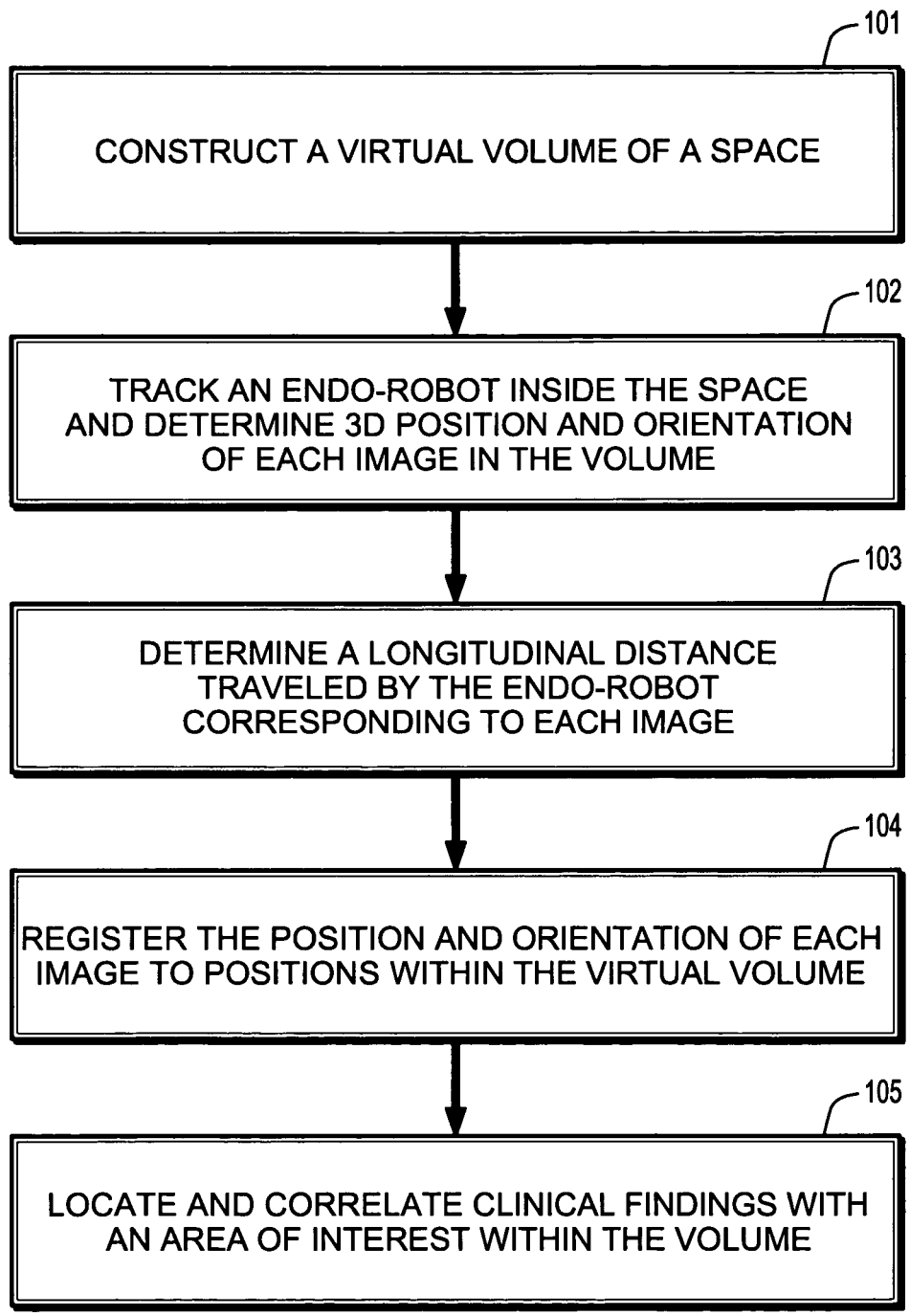
FIG. 1 is a flow chart of a method according to an embodiment of the present disclosure.

According to an embodiment of the present disclosure, images captured by an endo-robot can be registered to a reconstructed three-dimensional (3D) volume of data. The virtual volume is created based on a scan of a space 101, e.g., a colon (see FIG. 1). The endo-robot is tracked within the space and 3D position and orientation of every image captured by the endo-robot is determined 102. The longitudinal distance traveled inside the structure of interest, such as a colon, is determined 103. The position, orientation and longitudinal distance are used to register the position of the endo-robot to its corresponding position inside the 3D volume of data 104. Virtual endoscopy can be used to locate areas of interest and correlate clinical findings with the images of the areas of interest 105. The combined clinical findings can be used to improve diagnosis confidence, decrease the number of false positives, and decrease the number of biopsies performed. Such findings can also be used in various applications, for example, in the identification of patients with premalignant dysplasia in the colorectum, for example, using fluorescent imaging, enabling the identification of early neplasitc lesions in the colorectum, for example, using high-magnification endoscopy.

Figure 2:
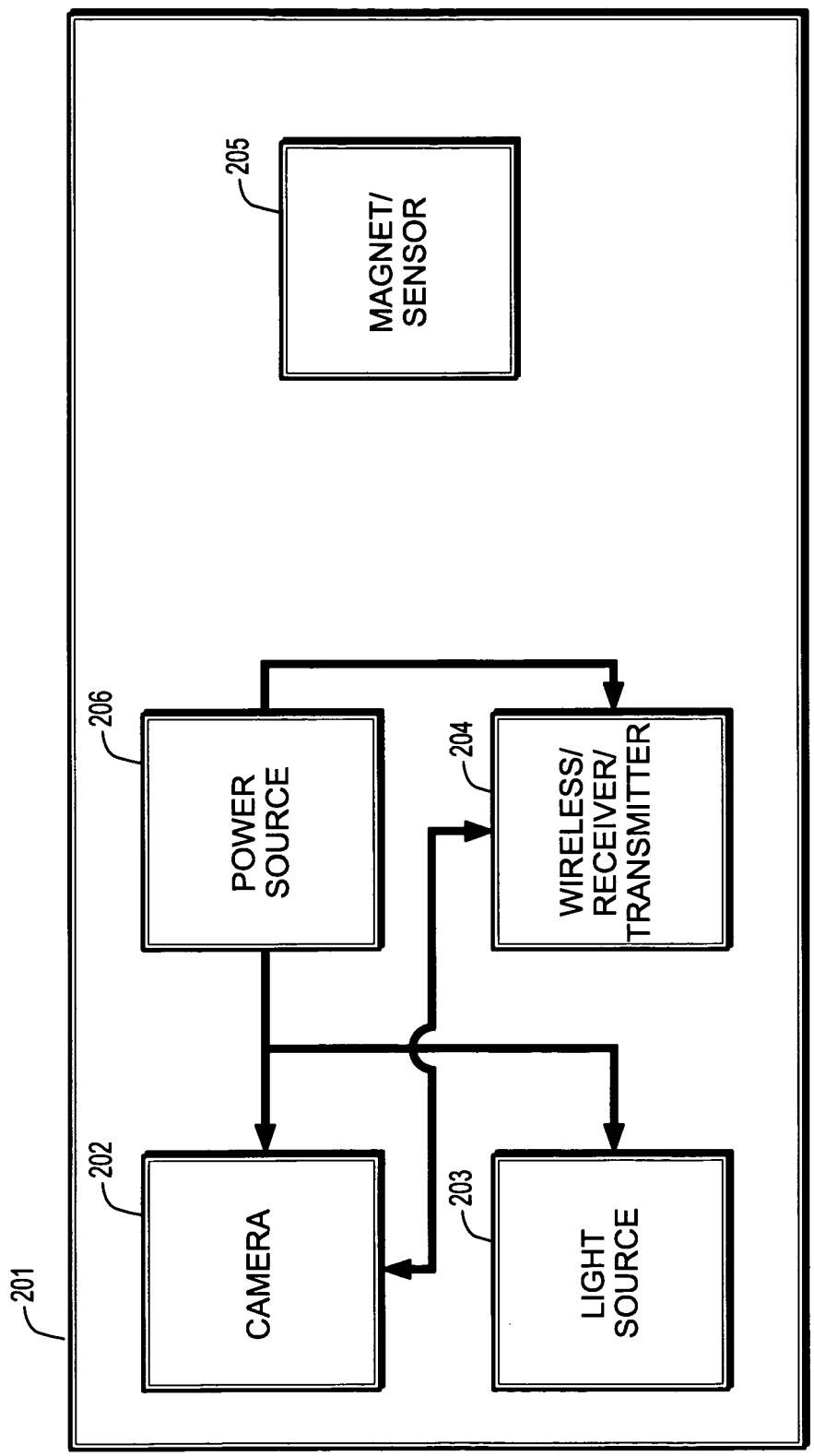
FIG. 2 is a diagram of an endo-robot according to an embodiment of the present disclosure.

Referring to FIG. 2, an endo-robot is a capsule 201 that can be swallowed or inserted non-surgically into a patient. Examples of such robots are those offered on the market by such companies as Given Imaging. These Capsules include a camera 202, an illumination source 203 and hardware for the wireless transmission of images 204 to a console outside the patient. The camera 202 acquires images or video images, e.g., macroscopic, normal-spectrum visualization, or which can perform fluorescent imaging, or magnification image or video capture.

Figure 3A:
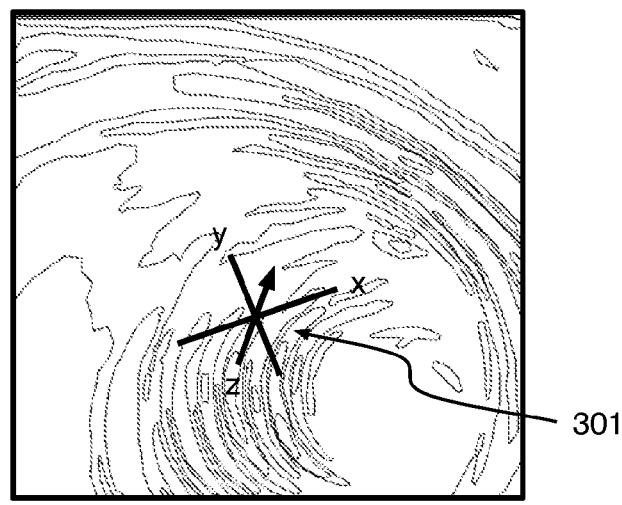
FIG. 3A is an illustration of a portion of a virtual endoscopy volume according to an embodiment of the present disclosure.
Figure 3B:
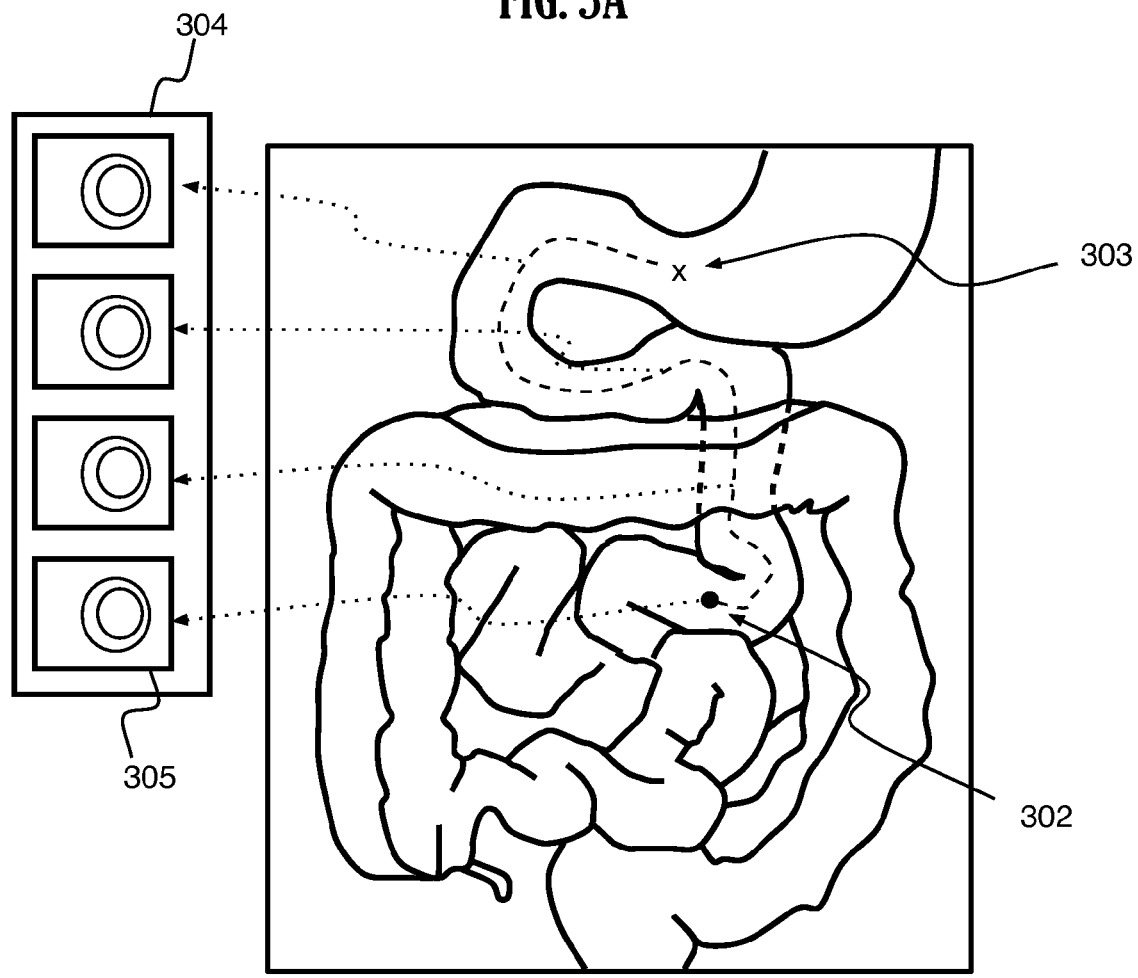
FIG. 3B is an illustration of a gastrointestinal tract and associated images according to an embodiment of the present disclosure.

The position, orientation and longitudinal distance associated with each captured image are used to register each image to a corresponding position inside the 3D volume of data. FIG. 3A illustrates a position and orientation of the endo-robot as an XYZ axis 301 within a virtual volume, wherein, for example, the Z-axis represents a sight line of the endo-robot camera 202. The longitudinal distance is determined, e.g., by tracking position over time, and associated with images 304 as illustrated in FIG. 3B. Thus, for portions of the 3D volume that may be positionally close, e.g., portions of the small intestine that fold on top of one another, the longitudinal distance can be used to distinguish between these portions, where a first portion 302 may be 0.5 meters from an initial point 303 and a second portion may be 2.5 meters from the initial point 303. An appropriate image, e.g., 305 is determined and displayed corresponding to an area of interest 302.

Another example of a tracking system includes an endo-robot having a tip electrode, a ring electrode and a location sensor. Location is determined determination using three coils placed outside the patient at known locations in three-dimensional space generating magnetic fields that decay as a function of distance. The location sensor measures the strength of a combined field, which enables a distance from each coil to be measured. The location of the sensor and thus the endo-robot is determined from the intersection of the fields whose radii are the distances measured by the sensor to the coils.

A power source 206 of the endo-robot can include a battery or inductor and battery. External powering can be realized through inductive charging using the inductor. For inductive charging the power source 206 is a secondary winding receiving charging power from a primary winding of an inductive charger. Inside the endo-robot, power is received with a coil and rectified by a diode. This direct-current (DC) voltage is used in charging a battery. External wireless supply of energy also allows for longer and more power-consuming procedures to be performed by the endo-robot.

The virtual endoscopy simulates an endoscopic intervention using methods of virtual reality and computer graphics. 3D volume data from CAT-scans, MRIs, 3D ultrasounds, rotations angiography or other sources can be used to generate a 3D view of the inside of the respective structures. 3D images may be created from two-dimensional (2D) computerized tomography (CT) or magnetic resonance (MR) data, for example, by volume rendering.

Registration may be performed using a predetermined reference frame or one or more user defined correspondences between captured images and the 3D volume that can form the basis for determining further correspondences. An example of a correspondence can be a landmark identifiable in the 3D volume and captured images such as the duodenojejunal flexure.

The position, orientation and longitudinal distance associated with each captured image are used to register each image to a corresponding position inside the 3D volume of data. FIG. 3A illustrates a position and orientation of the endo-robot as an XYZ axis within a virtual volume, wherein, for example, the Z-axis represents a sight line of the endo-robot camera 202. The longitudinal distance is determined, e.g., by tracking position over time, and associated with images 304 as illustrated in FIG. 3B. Thus, for portions of the 3D volume that may be positionally close, e.g., portions of the small intestine that fold on top of one another, the longitudinal distance can be used to distinguish between these portions, where a first portion 302 may be 0.5 meters from an initial point 303 and a second portion may be 2.5 meters from the initial point 303. An appropriate image, e.g., 305 is determined and displayed corresponding to an area of interest 302.

Figure 4:
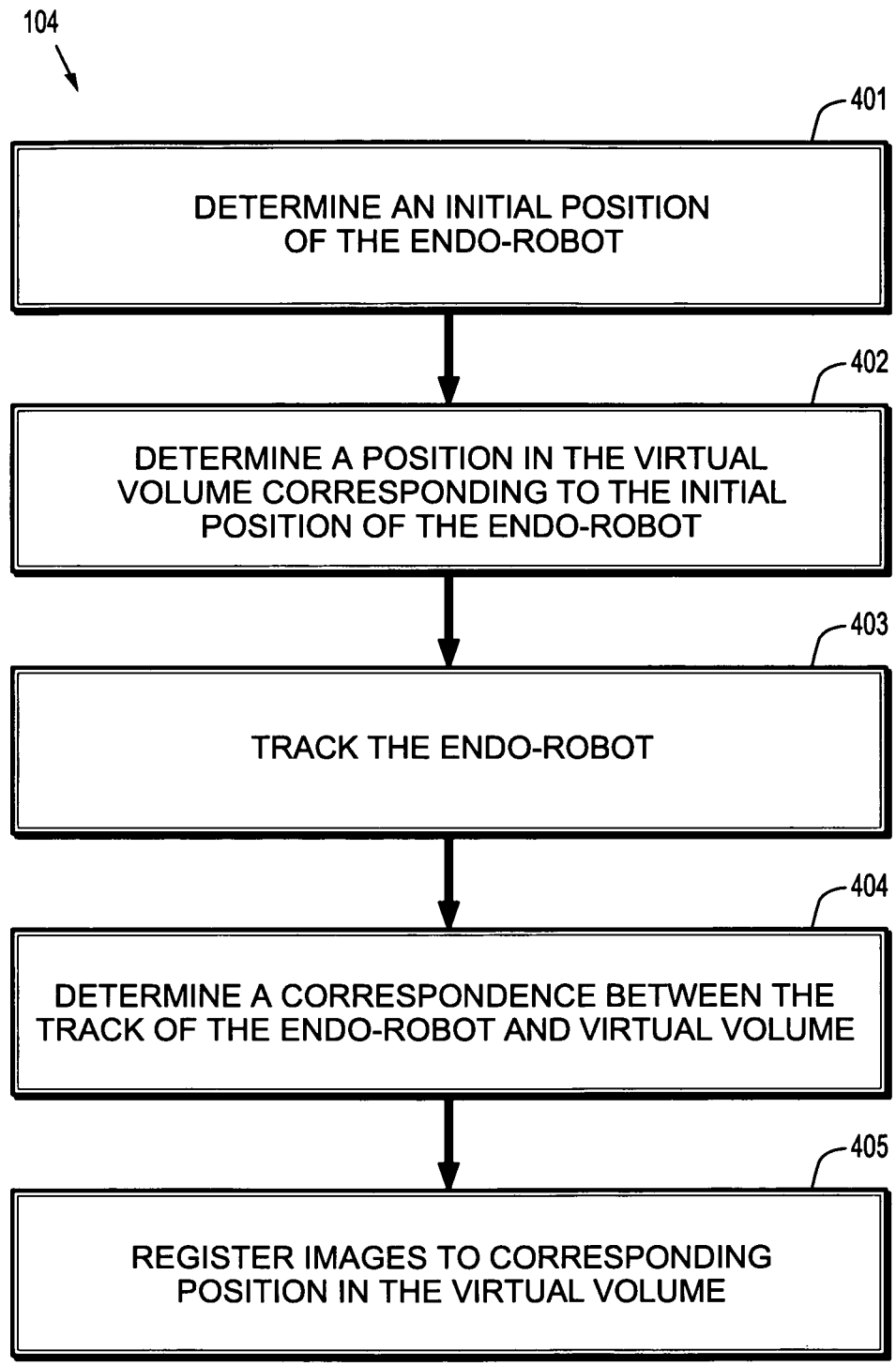
FIG. 4 is a diagram of a computer system according to an embodiment of the present disclosure.

Registration of images to the virtual volume can use a known starting position of the endo-robot and a position determined in the virtual volume. For example, tracking may begin from a patient's mouth, which is an identifiable location in the virtual volume. Referring to FIG. 4, registration includes determining an initial position of the endo-robot 401 and determining a position in the virtual volume corresponding to the initial position of the endo-robot 402. The endo-robot is tracked through a space 403, which is represented by the virtual volume. A correspondence of the track of the endo-robot is determined to the virtual volume in 3D space 404. Images captured by the endo-robot, having known positions and orientations along the track of the endo-robot are registered to corresponding positions within the virtual volume 405. The correspondence of the track of tracked course of the endo-robot (as depicted in FIG. 3B) to the virtual volume can use a centerline of a virtual volume determined from a scan of the patient. The centerline is automatically determined as part of commercially available CT and MRI scans as the track followed by a virtual fly-through of the virtual volume. The tracked course of the endo-robot and the determined centerline will correspond in three-dimensional space and may be registered manually or automatically based on comparative geometries.

The images captured by the endo-robot are registered to the volume renderings of the virtual volume. Because each image captured by the endo-robot is associated with spatial, directional and longitudinal information within the volume rendering, detailed images may be viewed of areas of interest identified in the volume rendering. Registered images can be automatically displayed as part of a fly-through of the virtual volume, for example, in a split screen configuration. The registered images can stored in memory, and can be accessed by a virtual rendering application executing by a computer, such that a virtual volume and real image may be displayed at the same time, for example, in two windows of an application or on two displays. Thus, a diagnosis, characterization and/or evaluation of a patient can be based on a virtual volume and a detailed registered image.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 5:
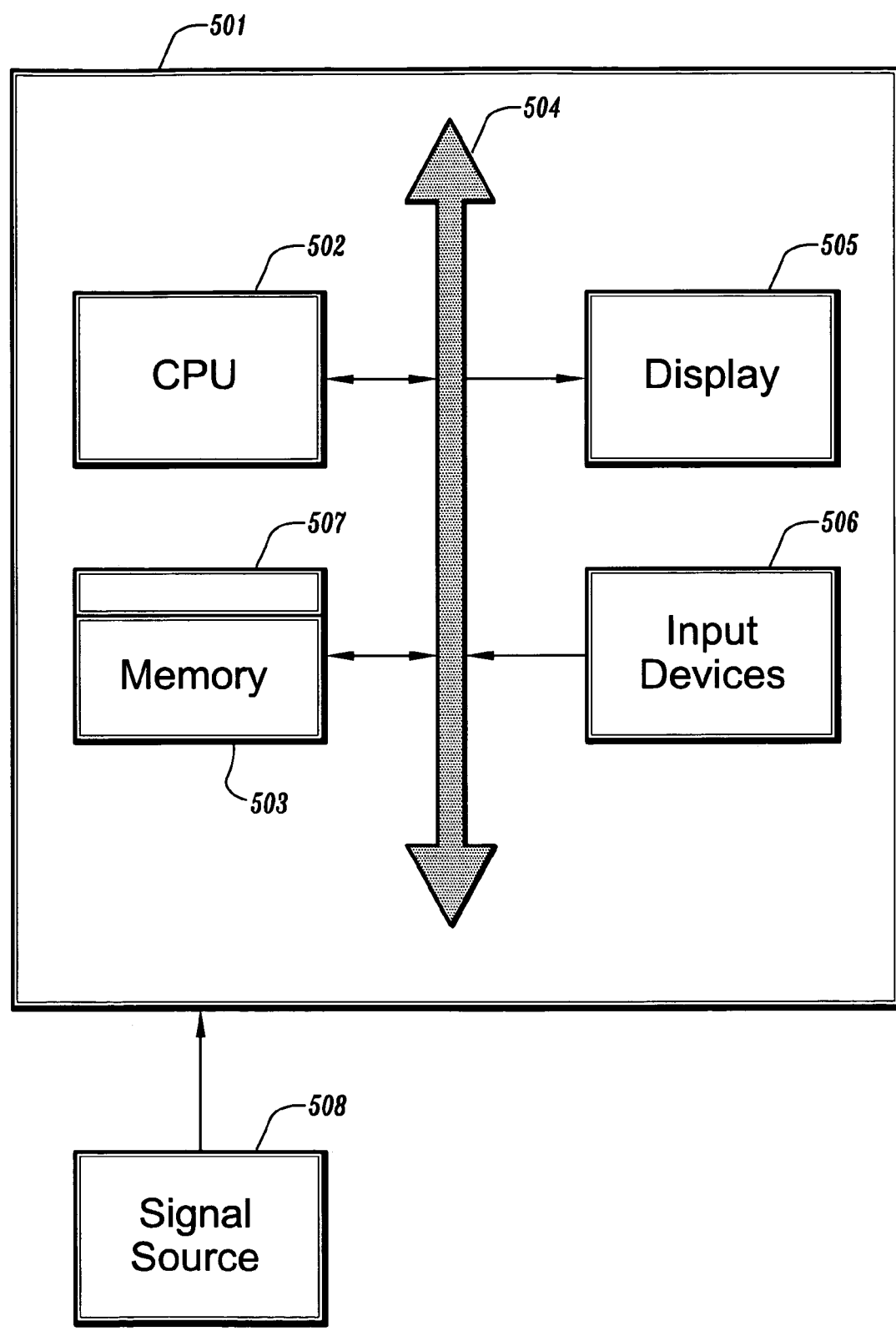

Referring to FIG. 5, according to an embodiment of the present invention, a computer system 501 for implementing the present invention can comprise, inter alia, a central processing unit (CPU) 502, a memory 503 and an input/output (I/O) interface 504. The computer system 501 is generally coupled through the I/O interface 504 to a display 505 and various input devices 506 such as a mouse and keyboard. The display 505 can display views of the virtual volume and registered images. The support circuits can include circuits such as cache, power supplies, clock circuits, and a communications bus. The memory 503 can include random access memory (RAM), read only memory (ROM), disk drive, tape drive, etc., or a combination thereof. The present invention can be implemented as a routine 507 that is stored in memory 503 and executed by the CPU 502 to process the signal from the signal source 508. As such, the computer system 501 is a general purpose computer system that becomes a specific purpose computer system when executing the routine 507 of the present invention.

The computer platform 501 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for virtual endoscopy using registered images captured by an endo-robot, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A computer-implemented method for associating an image with an area of interest in a three-dimensional volume comprising:
   modeling a volume as the three-dimensional volume;
   tracking an image capturing device within the volume, storing position and orientation information of the image capturing device at a time when at least one image is captured;
   determining a longitudinal distance traveled by the image capturing device at the time when the at least one image is captured;
   registering the position, orientation and longitudinal distance of the image capturing device to a corresponding position within the three-dimensional volume;
   determining an area of interest within the three-dimensional volume; and
   determining the at least one image registered to correspond to the area of interest, wherein the at least one image is displayed and the area of interest is characterized.

2. The computer-implemented method of claim 1, wherein registering further comprises:
   determining a centerline of the three-dimensional volume;
   determining a correspondence between a track of the image capturing device and the centerline of the three-dimensional volume, wherein the image capturing device is an endo-robot; and
   registering the at least one image to a position within the three-dimensional volume according to the correspondence.

3. The computer-implemented method of claim 1, wherein registering further comprises determining an initial position of the image capturing device and manually selecting a position corresponding to the initial position in the three-dimensional volume.

4. The computer-implemented method of claim 3, wherein the longitudinal distance is a distance of the image capturing device from the initial position.

5. The computer-implemented method of claim 1, wherein determining the at least one image comprises automatically displaying the at least one image in conjunction with the display of the corresponding position within the three-dimensional volume.

6. A non-transitory computer readable medium embodying instructions executed by a processor to perform method steps for associating an image with an area of interest in a three-dimensional volume, the method steps comprising:
   modeling a volume as the three-dimensional volume;
   tracking an image capturing device within the volume, storing position and orientation information of the image capturing device at a time when at least one image is captured;
   determining a longitudinal distance traveled by the image capturing device at the time when the at least one image is captured;
   registering the position, orientation and longitudinal distance of the image capturing device to a corresponding position within the three-dimensional volume;
   determining an area of interest within the three-dimensional volume; and
   determining the at least one image registered to correspond to the area of interest, wherein the at least one image is displayed.

7. The method of claim 6, wherein registering further comprises:
   determining a centerline of the three-dimensional volume;
   determining a correspondence between a track of the image capturing device and the centerline of the three-dimensional volume, wherein the image capturing device is an endo-robot; and
   registering the at least one image to a position within the three-dimensional volume according to the correspondence.

8. The method of claim 6, wherein registering further comprises determining an initial position of the image capturing device and manually selecting a position corresponding to the initial position in the three-dimensional volume.

9. The method of claim 8, wherein the longitudinal distance is a distance of the image capturing device from the initial position.

10. The method of claim 6, wherein determining the at least one image comprises automatically displaying the at least one image in conjunction with the display of the corresponding position within the three-dimensional volume.

* * * * *